United States Patent [19]

O'Rourke et al.

[11] Patent Number: 5,131,746
[45] Date of Patent: Jul. 21, 1992

[54] ON-LINE PROCESS CONTROL MONITORING SYSTEM

[75] Inventors: Patrick E. O'Rourke, Martinez, Ga.; David R. Van Hare, Aiken, S.C.; William S. Prather, Augusta, Ga.

[73] Assignee: The United States of America as represented by the United States Department of Energy, Washington, D.C.

[21] Appl. No.: 643,316

[22] Filed: Jan. 22, 1991

[51] Int. Cl.⁵ .................. G01J 3/42; G01N 21/05
[52] U.S. Cl. .................................. 356/319; 356/325; 356/436; 356/440
[58] Field of Search ............... 356/319, 325, 440, 436; 250/576, 227.11

[56] References Cited

U.S. PATENT DOCUMENTS

| | | | |
|---|---|---|---|
| 4,637,730 | 1/1987 | Ponstingl et al. | 356/411 |
| 4,663,961 | 5/1987 | Nelson et al. | 73/24 |
| 4,755,054 | 7/1988 | Ferree | 356/418 |
| 4,820,045 | 4/1989 | Boisde et al. | 356/319 |
| 4,822,168 | 4/1989 | Nogami et al. | 356/319 |
| 4,896,965 | 1/1990 | Goff et al. | 356/417 |
| 4,908,676 | 3/1990 | Bedell et al. | 356/72 |
| 4,989,942 | 2/1991 | Koenigsberg et al. | 250/576 X |
| 4,990,770 | 2/1991 | Hemmann et al. | 356/73.1 |

*Primary Examiner*—Vincent P. McGraw
*Attorney, Agent, or Firm*—Harold M. Dixon; William R. Moser; Richard E. Constant

[57] ABSTRACT

An on-line, fiber-optic based apparatus for monitoring the concentration of a chemical substance at a plurality of locations in a chemical processing system comprises a plurality of probes, each of which is at a different location in the system, a light source, optic fibers for carrying light to and from the probes, a multiplexer for switching light from the source from one probe to the next in series, a diode array spectrophotometer for producing a spectrum from the light received from the probes, and a computer programmed to analyze the spectra so produced. The probes allow the light to pass through the chemical substance so that a portion of the light is absorbed before being returned to the multiplexer. A standard and a reference cell are included for data validation and error checking.

7 Claims, 2 Drawing Sheets

ON-LINE PROCESS CONTROL MONITORING SYSTEM

The U.S. Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to systems for monitoring chemical processes. In particular, the present invention relates to fiber optic-based systems for monitoring in-line the concentrations of substances used in chemical processes.

2. Discussion of Background

Absorption spectrophotometry is one of the techniques which has long been recognized as adaptable for on-line chemical analysis. The technique is simple, relatively easy to interface with industrial and laboratory chemical processes, and can be selective and sensitive for analytes which absorb light.

Commercially available filter photometry devices provide reliable high-precision on-line data. These systems typically monitor two optical frequencies, one coincident with analyte absorption and the other at a point of no absorption. These devices automatically account for spectral baseline shifts, but are severely affected by interfering chromophores as well as changes in analyte absorptivity due to varying matrix conditions. More sophisticated spectrophotometric measurement devices which collect multiple channels of data can correct for some of these effects but, until recently, have been too complicated and delicate for process environments.

At the Savannah River Plant, several commercial two-wavelength filter photometers have been modified with fiber optic cables to monitor the elusion of neptunium and plutonium from anion exchange columns. Researchers at Oak Ridge National Laboratory developed a fiber optic photometer based on a rotating filter wheel to monitor the concentration of uranium and plutonium in process streams. Workers in France have developed similar analyzers using industrial photometers with as many as five measurement wavelengths. A multiplexed concentration analyzer has also been developed by the French using optical fibers and a commercial diode array spectrophotometer. This analyzer can monitor up to four sample locations in series acquiring data over the 400–800 nanometer range.

However, there remains a need for an on-line, fiber-optic-based apparatus for accurate, validated monitoring of chemical concentrations, an apparatus easily deployable at a large number of locations throughout a system and capable of rapid data acquisition and reduction.

SUMMARY OF THE INVENTION

According to its major aspects, the present invention is an apparatus for monitoring at a plurality of locations within an industrial or laboratory chemical processing system the concentrations of at least one chemical substance. The apparatus comprises a light source, a plurality of probes having lenses for directing light received via optic fibers through the chemical substance and returning it, again via optic fibers, after a portion of the light has been absorbed. A spectrometer receives the returned light and produces a spectrum which is analyzed by digital computer programmed for performing the analysis. Between the spectrometer and the light returning from each of the probes is a multiplexer that causes each of the probes to be sampled one at a time in series.

The multiplexer is a feature of the present invention. It allows rapid sampling of a large number of process cells and the reference and standard cells so that data from which concentration information can be derived is constantly being brought current. The advantage of this feature is that it eliminates duplicate apparatus for receiving and processing information from the various cells separately while still providing complete information.

The computer analysis of the received data is another feature of the present invention. The analysis makes use of the reference and standard cell input as well as stored data relating to absorptivity versus concentrations and various analytical techniques to adjust for baseline offset and to correct for interference and matrix effects and uses certain aspects of the data to indicate when substantial uncorrectable errors might be present. In comparison with laboratory measurement techniques, the present system performs equally well, both providing concentrations accurate to within 2%. The advantage of this analysis is that it makes slower laboratory techniques unnecessary for accurate work.

Another feature of the present invention is the use of standard compression fittings as process cells. The advantage of this feature is that it simplifies manufacturing and connection of the fiber optic cables.

Still another feature of the present invention is the use of a reference cell and a standard cell for data validation and error checking.

Other features and advantages of the present invention will be apparent to those skilled in the art of process control from a careful reading of the Detailed Description of a Preferred Embodiment accompanied by the following drawings.

DETAILED DESCRIPTION OF A PREFERRED EMBODIMENT

A laboratory or industrial chemical process system is a series of process vessels such as tanks, evaporators, and the like, joined by piping. Chemical processes take place in at least some of the vessels. Other processes such as precipitating, mixing, storing, evaporating, and so on, may take place in one or more of the other vessels.

Throughout the system, it will be important to know the concentration of one or more chemical substances. Parallel storage tanks, for example, may each hold a separate chemical substance that will be combined at a down-stream reaction vessel. The concentrations of the substances in the two tanks would be important to the proper reaction in the vessel and thus the concentrations of the two different substances must be monitored.

Figure 1:
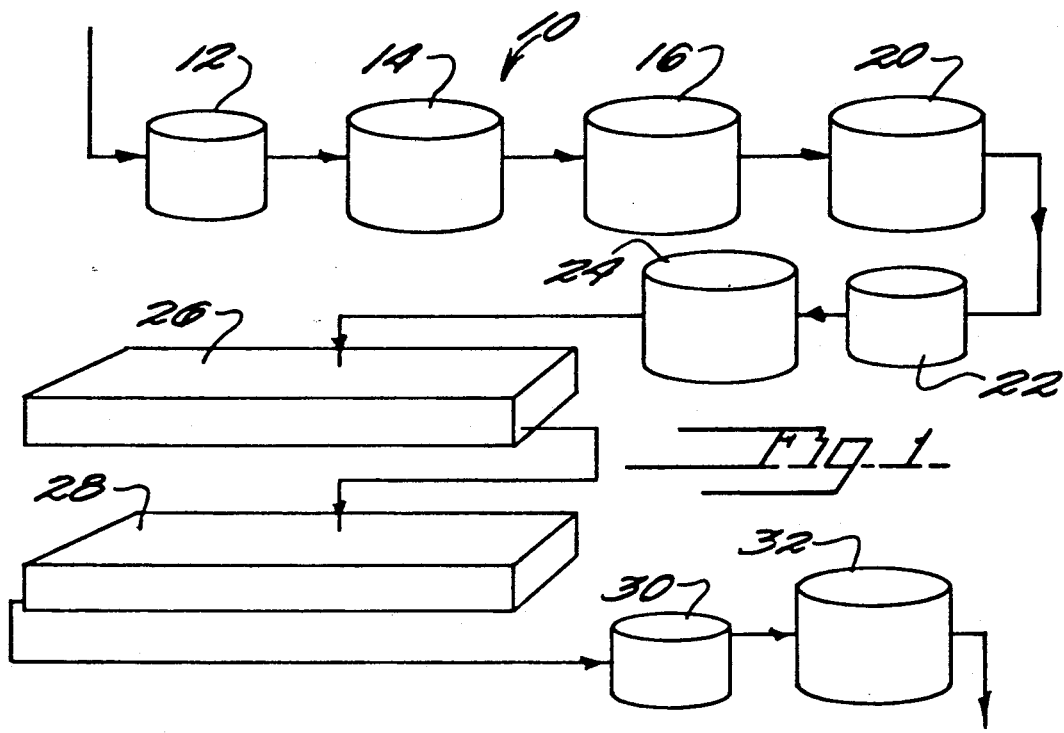
FIG. 1 is a schematic of a typical industrial chemical process.

FIG. 1 shows an example of a system, generally indicated by the reference number 10, having a number of tanks and vessels. Feed stock of a chemical substance flows into a first decanter 12 and thence to a first hold tank 14 and to a first feed tank 16. After feed tank 16, the chemical substance flows into an evaporator 20 and then a feed adjustment tank 22. From feed adjustment tank 22, the chemical substance will be moved to a second feed tank 24 and then to a first bank mixer/settler 26, then a second bank mixer/settler 28 and thence to a second decanter 30 and finally to a second hold tank 32 before exiting system 10. It is not important for the present invention to describe in detail what takes place in each of these tanks and vessels; system 10 is simply an example of a chemical process system having a number of locations where monitoring of the concentration of a substance is important. At first and second decanters 12, 30, first and second hold tanks 14, 32, first and second feed tanks 16, 24, and feed adjustment tank 22, monitoring cells can be positioned.

Figure 2:
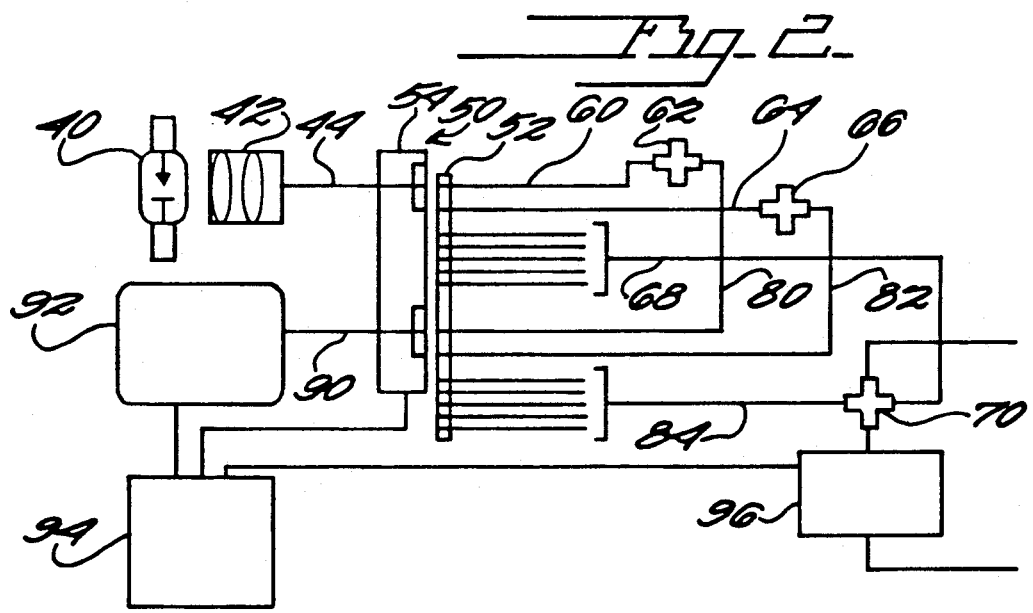
FIG. 2 is a schematic of a preferred embodiment according to the present invention.

Referring now to FIG. 2, which shows a schematic of the apparatus of the present invention, a source of light 40 is columated by a lens system 42 and directed into an optic fiber 44. Optic fiber 44 carries light from light source 40 to a multiplexer 50. Multiplexer 50 has two stages, a fixed stage 52 and a moving stage 54, in close proximity to each other. As moving stage 54 moves linearly with respect to fixed stage 52, the end of optic fiber 44 is aligned with one of a series of other optic fibers held in place on fixed stage 52.

One of these optic fibers, 60, leads to a reference cell 62. A second optic fiber 64 attached to fixed stage 52 leads to a standard cell 66. The remainder of optic fibers, collectively 68, lead to a plurality of process cells 70, one in each of the monitored tanks and vessels of system 10. Reference cell 62, standard cell 66, and process cells 70 will be described more fully below, however, each returns light in other optic fibers to multiplexer 50.

Reference cell 62 has a second optic fiber 80 leading to fixed stage 52 of multiplexer 50; standard cell 66 has a second optic fiber 82 leading to multiplexer 50; and process cells have a second optic fiber from each, collectively 84, leading to multiplexer 50. As moving stage 54 moves optic fiber 44 from light source 40, it also moves a third optic fiber 90 into and out of alignment with each of the second optic fibers coming from reference 62, standard 66, and process cells 70. The other end of third optic fiber 90 feeds into a spectrometer 92 which produces a spectrum from the light received. Spectrometer 92 passes spectral data to a computer 94 for analysis. In addition to analysis of spectral data computer 94 controls the movement of moving stage 54 of multiplexer 50 and directs the actions of a process sampler control 96.

For long distances, such as in excess of 15 meters, an external light source is required which has good stability and high brightness, rather than the internal light source of a typical spectrophotometer. Preferably, a Xenon arc lamp is used to provide these characteristics and suitable lighting up to 100 meters. A suitable lamp is made by Hamamatsu Corp., model number L2194. To reduce the effect of solarization on the optical fibers, light from the lamp is passed only when measurements are being made.

Optical fibers are preferably polymer-clad silica with high hydroxyl content for good UV response and, in a radioactive environment, good radiation resistance. Fibers having a nominal 600 micrometer core, for a good compromise between fiber flexibility and light-carrying capacity, plus a 750 micrometer polymer cladding and a 1060 micrometer ETFE buffer diameter are preferable. A suitable cable is manufactured by Applied Photonic Devices, which consists of a Belden #226101 Bitlite tight tube with Kevlar strength members and a PVC jacket.

A preferred multiplexer for use with the present invention is a stepper-motor-controlled linear translator. Although it is possible to reverse the fixed and moving stages, it is preferable to fix the stage with the most optic fibers connected to it and have just the single pair of optic fibers (from the lens and to the spectrophotometer) on the moving stage. The spacing between the optical fibers of the two stages should be kept very small, such as approximately 1 mm for a small transmission loss of about 2 dB at the fiber-to-fiber junction. A suitable multiplexer is made by Aerotech, Inc. which requires some customization for the desired number of optic fiber couplings, and has a switching time of less than one second for adjacent points.

Spectrophotometer 92 is preferably a photodiode array process analyzer. Other spectrometric technologies are also applicable, such as rapid scan grating and acoustic-optical filter instruments. A suitably rugged, single-beam device that has a fixed concave holographic grating and a 328 element array covering the 190-820 nm spectral region is made by Hewlett-Packard, model 8452. It has a built-in deuterium lamp which will prove satisfactory for shorter distances but is preferably replaced in favor of a brighter lamp as described above for longer distances.

To analyze the spectral data, a general purpose computer programmed for data analysis is required. Computer 94 is preferably also rugged and capable of operating in an industrial process environment that may be hot, dusty, electromagnetically "noisy", such as an IBM 7552 industrial computer.

Computer 94 is programmed with computational software and a model of analyte concentration information correlated with measured absorption spectra. Known concentrations are assumed to be linearly related to input data. Computational analyses include calculations of Partial Least Squares, Principle Component Regression, Classical Least Squares, and Multiple Linear Regression analyses. The first two of these are similar in that both model spectral data sets by constructing orthogonal vectors to describe the variance between the spectra in the set. In Principle Component Regression analysis, vectors are chosen to minimize error in the spectral data. An unknown spectrum can then be easily decomposed to eigenvalues corresponding to each of the principal component regression vectors. In the case of building a model for concentrations, the eigenvalues of spectra in a calibration data set are correlated with their known concentration by any of a number of methods such as Multiple Least Squares.

In Partial Least Squares analysis, however, the vectors are chosen to minimize error in the given concentrations, rather than in the spectral data as with Principle Component Regression, thus building the concentration model as new vectors are computed. This often reduces the number of vectors required to model concentrations and reduces the amount of "noise" incorporated into the results. But the disadvantage is that Partial Least Squares analysis assumes a linear relationship between the data and the concentrations. Partial Least Squares analysis calculates the concentrations from an unknown spectrum by first computing likenesses between the spectrum and the orthogonal vectors, and then summing the contribution to the concentration from each of the vectors. Spectrum residuals are computed by subtracting the likenesses of the vectors from the original spectrum. The number of vectors used to describe a given chemical system is determined by minimizing the predicted error of a set of spectra with known concentrations. This verification set should, of course, not be part of the set used to build the model.

Figure 3:
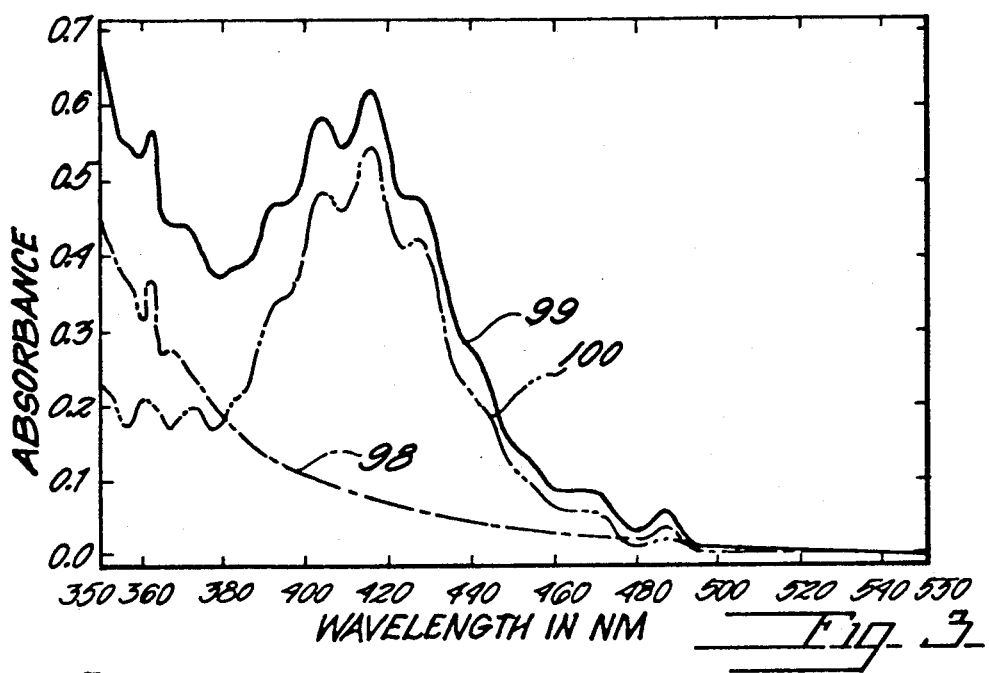
FIG. 3 is a graph of absorbance versus wavelength for a spectrum measured by a flow cell, a spectrum in an empty cell and the net spectrum.

FIG. 3 illustrates the absorption spectra of an empty cell 98 and the measured spectrum 99 from a cell through which a chemical substance is flowing. The net spectrum 100 is obtained by subtracting the measured spectrum from the empty cell spectrum.

Figure 4:
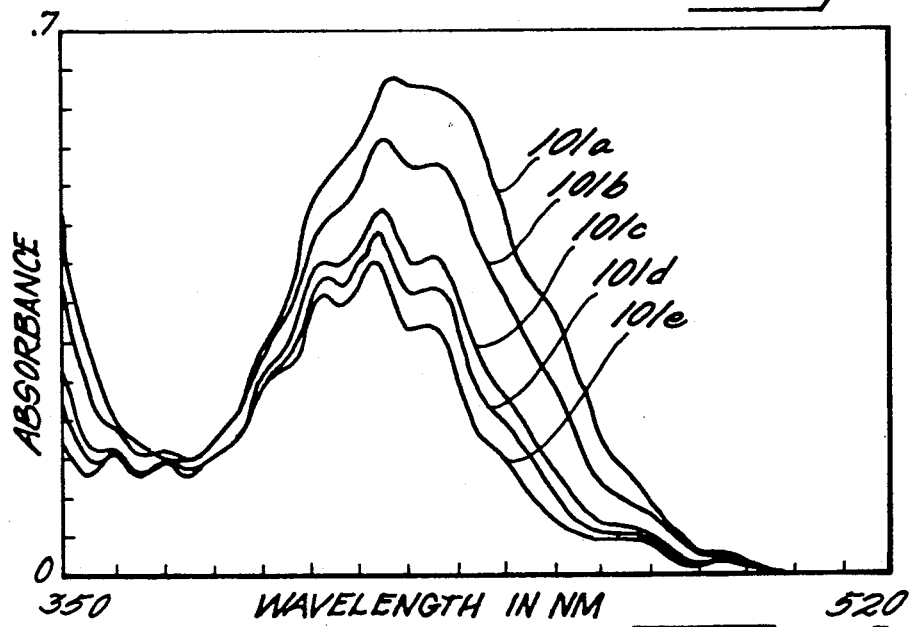
FIG. 4 is a graph of absorbance versus wavelength for various concentrations of a chemical substance.

In FIG. 4, several net spectra are shown, each corresponding to a different concentration of a chemical substance. Spectra 101a, 101b, 101c, 101d, 101e correspond to 6.0, 4.0, 2.0, 1.0, and 0.1 molar concentrations, respectively.

Figure 5:
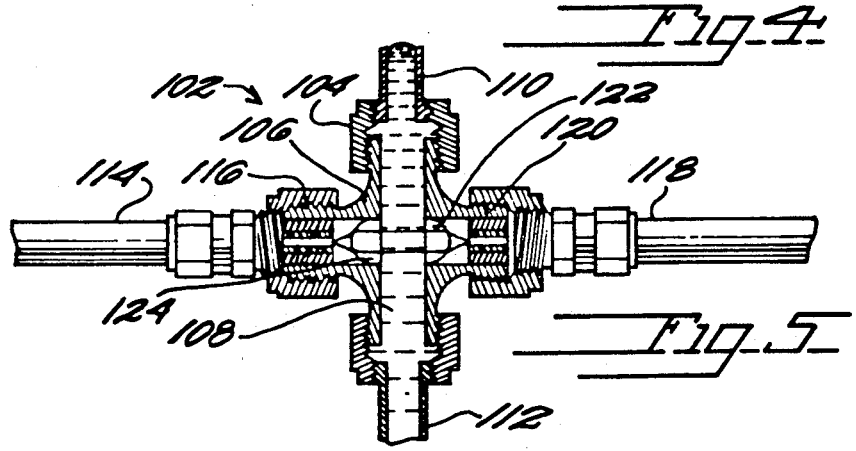
FIG. 5 is a cross sectional side view of a typical process cell.

As illustrated in FIG. 5, a process cell 102 is a probe 104 with a probe body 106 having an interior 108 with two connections 110, 112 to allow the chemical substance to flow in and out and a third connection 114 for a first optic fiber 116 bringing light into the probe interior 108 and a fourth connection 118 for a second optic fiber 120 to carry the light, following absorbance of a portion of the light, from probe 104. Probe body 106 holds the first and second optic fibers 116, 120 spaced apart so that the chemical substance can flow therebetween. Two lenses 122, 124, preferably planoconvex direct light from optic fiber 116, across the chemical substance, and into second optic fiber 120.

Standard cell 62 is similar to probe 104. However, it has an interior cavity filled with the chemical substance at a known standard concentration. Reference cell 66 is an empty, or blank cell, also similar to probe 104.

In use, blank and standard cells are measured, then each of the process cells is monitored. Rapid acquisition and averaging methods are necessary to ensure that only valid data from flowing chemical substance streams are used to calculate concentrations. At each multiplexer position, fifteen one-tenth second spectra are collected. If the baseline offset of a spectrum is less than a predesignated cutoff value, the spectrum is included in the calculation of the average and variance spectra. The magnitude of the variance spectrum is indicative of flow through the process cells. Disturbances in the flowing stream cause fluctuations in baseline offsets which are typically 10 to 100 times the variance of static solutions. If the variance at a process location is less than five times the variance at the standard, the sampler may be plugged and suitable warning should be given by the computer to the apparatus operator.

To eliminate variable baseline effects, concentrations and the residual spectrum can be computed from the second derivative of the average spectrum. The residual spectrum is the absorbance left in the collected data for which the model cannot account. The magnitude of the residual spectrum is a sensitive indicator of the quality of the calculated concentrations. For standards, the ratio of the magnitude of the residual to the magnitude of the average residual (from the Partial Least Squares model) is near one. If an unknown interference is present the ratio of residual to average residual is much greater than one provided the signal-to-noise ratio of the spectrum is much greater than one.

It will be apparent that many changes and modifications can be made in the preferred embodiment described above without departing from the spirit and scope of the invention which is defined by the appended claims.

What is claimed is:

1. Apparatus for monitoring at a plurality of locations within a system the concentrations of at least one chemical substance involved in a chemical process, said apparatus comprising:

a source of light;

plurality of process cells for directing said light through a sample of said at least one chemical substance so that said chemical substance can absorb a portion of said light, each of said process cells having an interior through which light from said source of light is directed;

first means for carrying said light, said first carrying means carrying said light from said source of light to each of said plurality of process cells;

second means for carrying said light, said second carrying means carrying said light after said portion of light has been absorbed by said at least one chemical substance from each of said plurality of process cells;

means for producing a spectrum from said light received by said second carrying means, said producing means in optical communication with said second carrying means;

multiplexing means for selecting one process cell of said plurality of process cells at a time so that said producing means can produce a process spectrum from said one cell of said process cells;

a reference cell for producing a reference spectrum for comparison to said process spectrum, said reference cell having an interior containing none of said chemical substance and directing said light from said source of light through said interior;

a standard cell for producing a standard spectrum for comparison to said process spectrum, said standard cell having an interior containing a known concentration of said chemical substance and directing said light from said source of light through said interior; and means for comparing said reference spectrum, said standard spectrum and said process spectrum and determining said concentration of said chemical substance in said process cell.

2. The apparatus as recited in claim 1, wherein said source of light operates when said producing means is producing said spectrum and does not operate when said producing means is not producing said spectrum.

3. The apparatus as recited in claim 1, wherein said multiplexing means comprises a fixed stage and a movable stage, said process cells connected to said fixed stage.

4. The apparatus as recited in claim 1, wherein said second carrying means and said producing means are connected to said multiplexing means and said multiplexing means comprises a fixed stage and a movable stage, said second carrying means is connected to said fixed stage, said fixed stage and said movable stage being spaced so that said fixed stage and said movable stage are approximately not more than 1 mm apart.

5. The apparatus as recited in claim 1, wherein said producing means collects a plurality of spectra from each process cell before another process cell is selected by said multiplexing means.

6. The apparatus as recited in claim 1, wherein said first and said second light carrying means both further comprise polymer-clad silica optic fibers.

7. The apparatus as recited in claim 1, wherein said source of light is a xenon arc lamp.

* * * * *